United States Patent [19]

Yoshimatsu et al.

[11] Patent Number: 5,365,941
[45] Date of Patent: Nov. 22, 1994

[54] APPARATUS FOR DETECTING SMALL INVOLUNTARY MOVEMENT

[75] Inventors: Hiroshi Yoshimatsu, Kanagawa; Shinji Murakami, Hokkaido; Mitsuho Yamada, Tokyo; Kenya Uomori, Osaka; Hitoshi Hongo, Gifu; Keiichi Ueno, Tokyo; Mitsuru Fujii, Hokkaido; Norihito Nakano, Hokkaido; Jiro Miyazawa, Hokkaido; Ryo Fukatsu, Hokkaido; Naohiko Takahata, Hokkaido, all of Japan

[73] Assignee: ATR Auditory and Visual Perception Research Laboratories, Kyoto, Japan

[21] Appl. No.: 76,047

[22] Filed: Jun. 16, 1993

[30] Foreign Application Priority Data

Nov. 27, 1992 [JP] Japan .................................. 4-318423

[51] Int. Cl.$^5$ ............................................. A61B 13/00
[52] U.S. Cl. .................................................. 128/745
[58] Field of Search ....................... 128/745, 774, 782; 351/229

[56] References Cited

U.S. PATENT DOCUMENTS

| | | |
|---|---|---|
| 4,582,403 | 4/1986 | Weinblatt . |
| 4,854,329 | 8/1989 | Walruff ................................ 128/745 |
| 4,889,422 | 12/1989 | Pavlidis ............................... 128/745 |
| 5,070,883 | 12/1991 | Kasahara ............................. 128/745 |

FOREIGN PATENT DOCUMENTS

| | | |
|---|---|---|
| 0487855 | 6/1992 | European Pat. Off. . |
| 09017705 | 11/1991 | WIPO ................................. 128/745 |

OTHER PUBLICATIONS

Proceedings of the Annual International Conference of the IEEE Engineering in Medicine and Biology Society, vol. 13, No. 4/5, 3 Nov. 1991, Orlando, USA, pp. 1513–1515, H. Yoshimatsu et al., "High Dimensional Chaos of Miniature Eye Movements".

SMPTE Journal, vol. 95, No. 12, Dec. 1986, White Plaines, USA, pp. 1230–1241, M. Yamada et al., "Quantitative Evaluation of Eye Movements as Judged by Sight-Line Displacements".

N. B. Abraham, "Calculating the Dimension of Attractors from Small Data Sets", Feb. 24, 1986, pp. 217–221.

W.N. Charman, "Fluctuations in Accommodation: A Review", Apr. 1988, pp. 153–164.

Thomas C. Halsey, "Fractual Measures and their Singularities: The Characterization of Strange Sets", Feb. 1986, pp. 413–423.

S.F. Stanten, "A Statistical Analysis of Pupil Noise", Jul. 1966, pp. 140–152.

*Primary Examiner*—Max Hindenburg
*Attorney, Agent, or Firm*—Lowe, Price, Leblanc & Becker

[57] ABSTRACT

A target is presented on a board for calculation, eye movement of a subject while he is gazing at the target is detected by an eye movement detecting portion, the output of which is converted into a digital signal in a signal processing circuit and it is applied to a calculating portion. The calculating portion calculates small involuntary movement data in response to the input digital signal to find a value of a fractal dimension and time dependence of the fractal dimension to determine a disease related to brain function, and the output of determination is provided from an output portion such as a printer.

11 Claims, 7 Drawing Sheets

FIG. 10(a)
XYZ COORDINATE SYSTEM

FIG. 10(b)
POLE COORDINATE SYSTEM

FIG. 11

APPARATUS FOR DETECTING SMALL INVOLUNTARY MOVEMENT

BACKGROUND OF THE INVENTION

1. Field of the Invention

The present invention relates to an apparatus for detecting small involuntary movement. More specifically, the present invention relates to an apparatus for detecting small involuntary movement by measuring the line-of-sight of a subject and calculating a fractal dimension, for detecting defects in brain function and in eye movement control mechanism of the subject.

2. Description of the Background Art

The number of patients suffering from Alzheimer's disease is estimated to be four million in the United States and about a million in Japan. Compared with senile dementia such as cerebrovascular disease popular among Japanese, the cause of Alzheimer's disease is not known, and much effort has made to find the cause so as to enable early diagnosis and early medical treatment. However, it is difficult to discriminate Alzheimer's disease from cerebrovascular disease when there is no typical symptoms. There has been a strong demand of accurate method of discrimination, since development of disease, pharmaceutical treatment and so on are different for these diseases.

Hachinski's ischemic score has been proposed as a method of discriminating these two diseases. According to this ischemic score, a point is given dependent on whether or not the patient has an anamnesis of apoplexy, cerebral infraction or the like and if the points exceed a prescribed number, it is determined as the cerebrovascular disease, and otherwise it is determined to be Alzheimer's disease. However, discrimination is still difficult by this method if the patient has no such anamnesis.

It has been known that neuropsychological symptom which is considered to be an impairment of "tool function" such as visual cognitive dysfunction appears from relatively early period of Alzheimer's disease. In view of this fact, Fujii et al. has reported the following analysis carried out by utilizing eye movement. More specifically, a problem of copying a cube on the right side while watching an original of the cube on the left side is presented. Even a patient who is in the initial stage I of Alzheimer's disease and does not show apparent constructional apraxia is reported to show characteristic symptom similar to a so called Balint syndrome; that is, the patient cannot stare at one point, or more specifically, abnormal distribution of gazing point appears, saccade deviated from both the presented cube and the depicted drawing by the patient is generated, or the point of gazing is fixed at the same point for a long period of time. In Alzheimer's disease, it is supposed from MRI (nuclear magnetic periorbital inspection) that there is caused dysfunction of parietal lobe which is related to spatial vision. Accordingly, constructional dysfunction derived from degradation in function of the rear association areas with the parietal lobe being the center, degradation of function of positional recognition of a target point or recognition of depth derived from dysfunction of external spatial vision such as dysfunction of eye movement, dysfunction of coordinate transformation system between the coordinate of eye movement system and the coordinate of the center of one's body axis, or visual-motor dysfunction, is supposed to be a possible cause of the aforementioned symptoms.

SUMMARY OF THE INVENTION

Therefore, an object of the present invention is to provide an apparatus for detecting small involuntary movement allowing easy determination of diseases related to brain function, in which the movement of line-of-sight realized by the eye movement of the subject is noted.

Briefly stated, the present invention provides an apparatus for detecting small involuntary movement for determining a disease related to brain function by detecting eye movement of a subject, in which a target is presented to the subject, based on the time-change of the movement of the line-of-sight derived from the eye movement detected by eye movement detecting means while the subject is gazing at the target, abnormality in small involuntary movement component is discriminated by using fractal dimension analysis, and whether or not the subject is suffering from a disease related to brain function is determined.

Therefore, according to the present invention, abnormality of the eye movement control mechanism in the brain of the subject can be easily detected, which facilitates discrimination of cerebrovascular disease from Alzheimer's disease.

In a preferred embodiment of the present invention, head movement of the subject while the subject is gazing at a target is detected, based on the detected head movement and on eye movement, movement of the line-of-sight is calculated, and based on the movement of the line-of-sight, abnormality in the small involuntary movement component is discriminated.

In a more preferred embodiment of the present invention, small movement or flicks is found on the basis of time-change of the detected movement of the line-of-sight, a fractal dimension is calculated corresponding to the flicks, and characteristics of the eyeball control system is quantified corresponding to the calculated fractal dimension.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
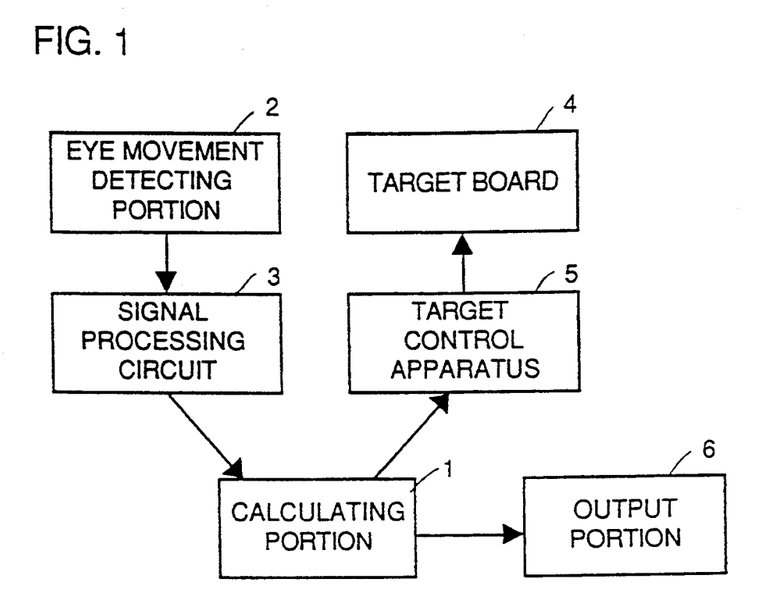
FIG. 1 is a schematic block diagram of one embodiment of the present invention.

FIG. 1 is a schematic block diagram of one embodiment of the present invention. Referring to FIG. 1, an eye movement detecting portion 2 detects eye movement of a subject, detection output thereof is converted to a digital signal at a signal processing circuit 3 and it is applied to a calculating portion 1. The calculating portion 1 applies a control signal to a target control apparatus 5 so as to present a target on a target board 4. A light emitting diode may be used as the target. The calculating portion 1 calculates small involuntary movement data on the basis of the detection output detected by eye movement detecting portion 2 while the subject is gazing at the target presented on the board 4, calculates a value of a fractal dimension and time dependence of the fractal dimension, determines disease related to brain function, and applies the determination output to an output portion 6. A display apparatus or a printer may be used as the output portion 6.

Figure 2:
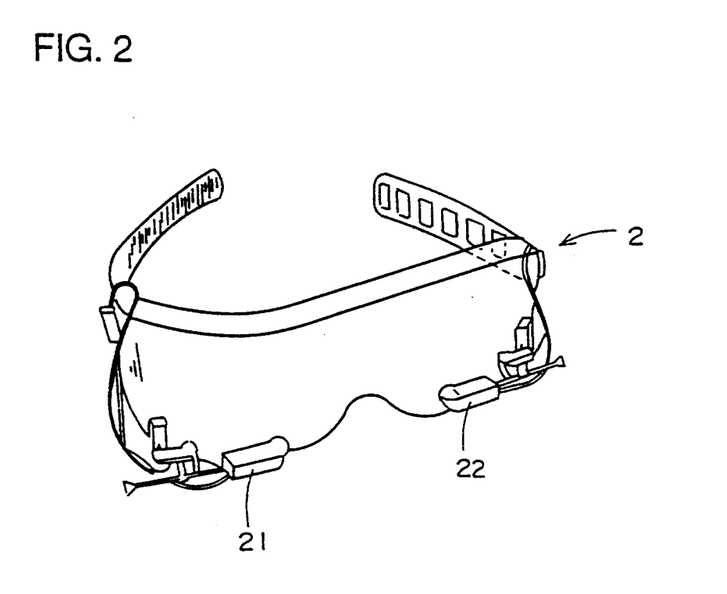
FIG. 2 shows an example of the eye movement detecting portion shown in FIG. 1 attached to goggles.
Figure 3A:
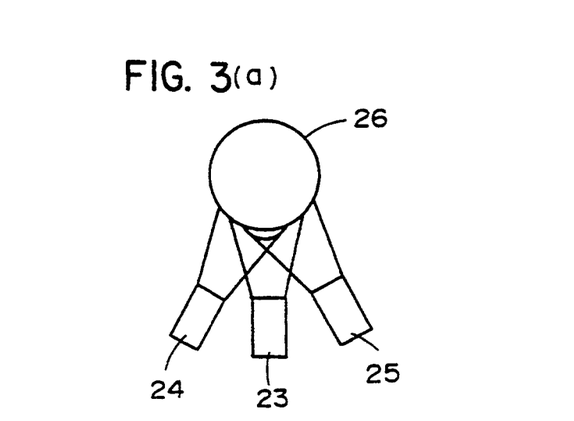
FIGS. 3(a)–3(c) show a specific example of the eye movement detecting portion.
Figure 3B:
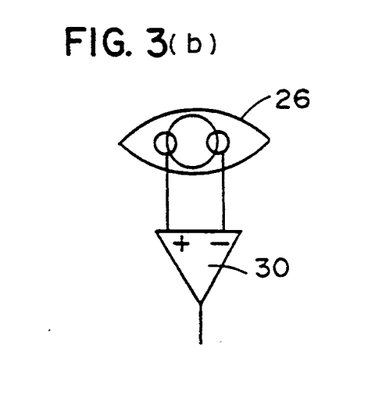
Figure 3C:
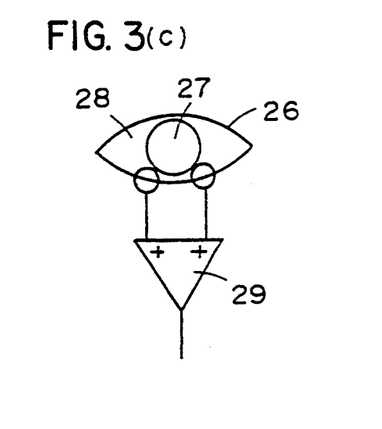

FIG. 2 shows an example of the eye movement detecting portion shown in FIG. 1 attached to goggles, and FIG. 3 shows a specific example of the eye movement detecting portion 2.

The subject wears the goggles shown in FIG. 2, at lower portions of which eye movement detecting portions 21 and 22 are attached. The detecting portions 21 and 22 each include a light emitting diode 23 provided at center and photodiodes 24 and 25 provided on both sides of the diode 23, as shown in FIG. 3. A light emitting diode radiating infrared rays having relatively wide directivity of about ±21° C. is used as the light emitting diode 23, while ones having acute directivity of about ±10° C. are used as the photodiodes 24 and 25. The light beam emitted from the light emitting diode 23 to the eye ball 26 is reflected from the iris of the eye 27 and from the white of the eye 28 with different reflectivity, and the difference in reflectivity is amplified by an operational amplifier 29. If the difference is calculated, a horizontal output (left and right) is obtained as shown in FIG. 3(b), and if the sum is calculated by an operation amplifier 30, a vertical (up and down) output is obtained as shown in FIG. 3(c).

Figure 4:
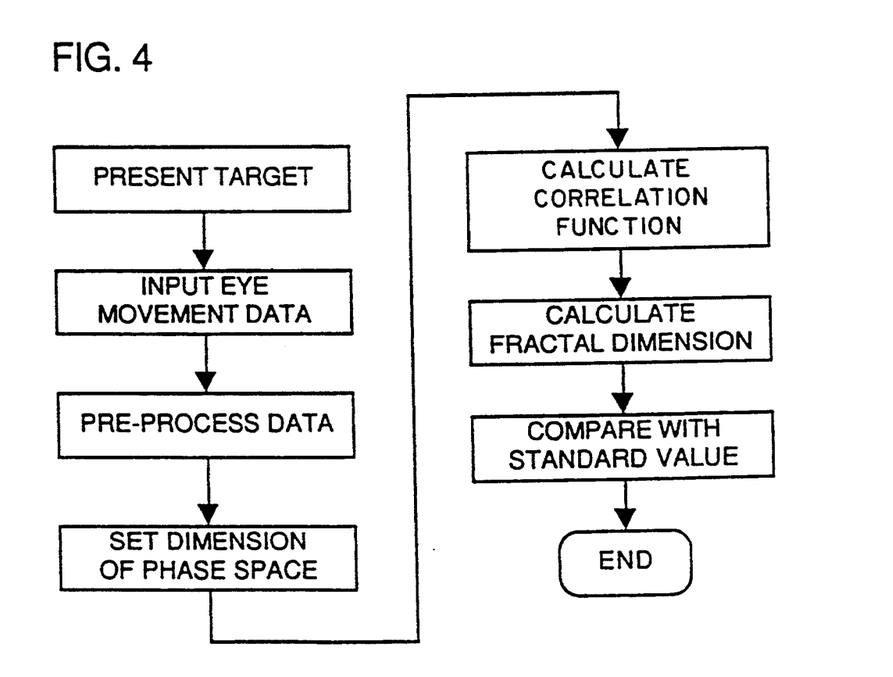
FIG. 4 is a flow chart showing the operation of one embodiment of the present invention.
Figure 5:
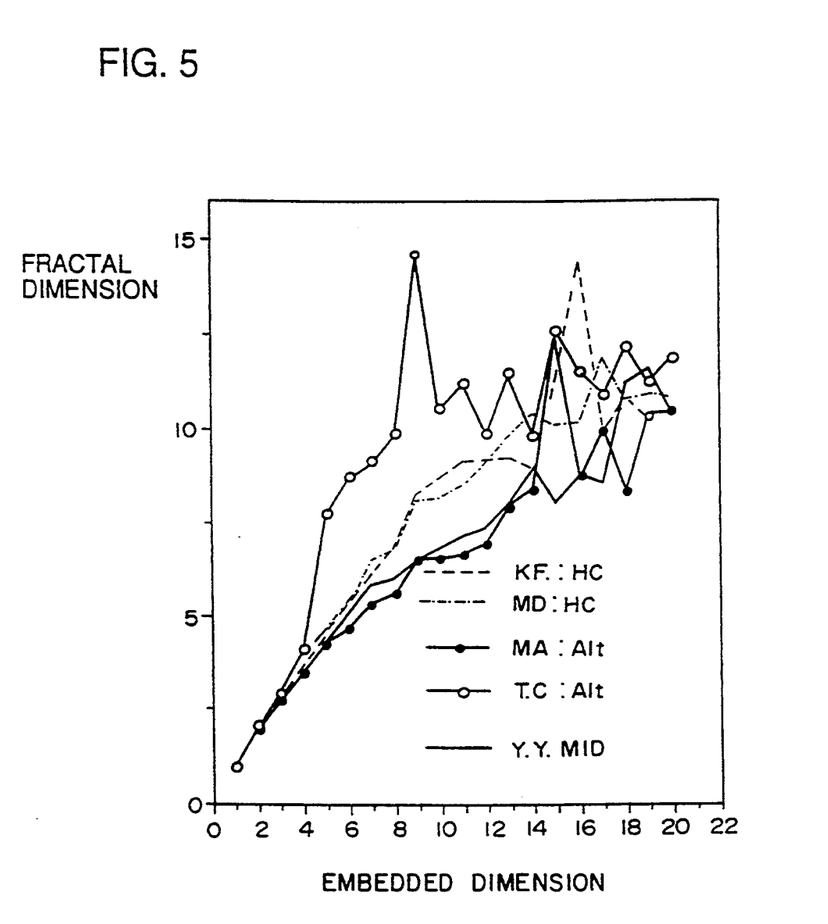
FIG. 5 shows embedding dimension dependence of a fractal dimension, as an example of analysis in accordance with one embodiment of the present invention.

FIG. 4 is a flow chart showing an operation of one embodiment of the present invention, and FIG. 5 shows a result of discrimination in accordance with one embodiment of the present invention.

A specific operation of one embodiment of the present invention will be described with reference to FIGS. 1 to 5. First, the subject wears eye movement detecting portion 2 shown in FIG. 2 on his head. A chin-rest or the like is used to fix the head of the subject. Calculating portion 1 applies a control signal to target control portion 5 so as to light the light emitting diode on target board 4. While the subject is gazing at the target on the board 4, the eyeball 26 is irradiated with infrared ray from a light emitting diode 23 shown in FIG. 3, and light reflected from the black of the eye and from the white of the eye are received by photodiodes 24 and 25. Photosensitive outputs from photodiodes 24 and 25 are digitized by a signal processing circuit 3, and then applied to calculating portion 1 as eye movement data.

Calculating portion 1 accepts the digitized eye movement data as time-serial two-dimensional sampling data. The two-dimensional data herein corresponds to coordinates of arbitrary coordinate system, that is, a polar coordinate system or orthogonal coordinate system. Calculating portion 1 provides a fractal dimension of the small involuntary eye movement, assuming that one of these coordinate axes being x (t). As a method of calculating fractal dimension with simplification by employing time-serial sampling data, there is a method described, for example, in N. B. Abraham et al: Phys. Lett., Vol 144A (5). pp. 217–221 (1986). For preliminary processing, calculating portion 1 assumes time-serial one dimensional data as x (t), selects an appropriate sampling period from the data, and generates discrete data $\{x_i = x(t_i) : i = 1 \ldots n\}$.

Then, calculating portion 1 sets dimension of a phase space. Namely, $$X_1(i) = (x_i, x_{i-1})$$

where $X_i$ which is to be paired with $x_i$ is generated with the value of i being $i = 1, 3, \ldots, 2n+1, \ldots, N-1$. An orbit on a pseudo-phase space is topologically equivalent to (x (t), v (t)) on phase space, where v (t) is time differential (velocity) of x (t).

Then, calculating portion 1 calculates correlation dimension. In accordance with the method of N. B. Abraham et al., a correlation dimension defined as follows is calculated as the fractal dimension, with respect to a data point set on the pseudo-phase space.

Definitions of correlation dimension:

$$frac.\ dim = log\ (C\ (r))/log\ (r)$$

where C (r) is correlation function, and r is a distance between the respective data points.

$$C(r) = lim 1/N^2 \cdot N_i N_j H(r - |x_i - x_j|)$$

where xi is the position of a measured point at time ti, and H (r) is Heaviside step function.

The small involuntary movement is measured in this manner, the fractal dimension is calculated, the value of the fractal dimension is compared with a pre-measured standard value of a healthy person or the value of a patient, and the result is displayed on a display apparatus or printed out by a printer. The result is such as shown in FIG. 5. FIG. 5 shows, as an example of analysis, dependence of fractal dimension on embedding dimension, in which the abscissa indicates embedded dimension of information space, and the ordinate indicates the fractal dimension. Examples of patients suffering from Alzheimer's disease are represented by M. A. and T.C. The patient T.C. suffering from Alzheimer's disease changed his attitude during experiment and detection was failed. In such an example, it is surely known that the result is apparently different from the results of successful experiments of healthy persons and patients. With respect to the embedded dimension dependence of the fractal dimension, the result of a healthy person HC (examples of K.F., M.D) is compared with the result of patients suffering from Alzheimer's disease M. A., Y.C. or with the result of a patient Y.Y., suffering from MID, and it can be seen that the dependence is higher at higher embedded dimension in case of healthy person. In addition, significant difference is quantitatively recognized when the result of a patient M.A. suffering from Alzheimer's disease is compared with the result of a patient Y.Y. suffering from MID.

The fractal dimension of a patient suffering from a disease related to brain function is low, since, qualitatively, the locus of small involuntary movement is more one-dimensional than the two-dimensional movement of a healthy person as micro saccades in the horizontal direction occurs frequently. It may be sometimes difficult to discriminate the patient suffering from the disease related to brain function from a healthy person or a patient MID because of personal error. However, when this method is used in addition to the conventional Hachinski's ischemic score as well as computer tomography of the brain, almost perfect discrimination becomes possible.

In the meantime, the fractal dimension may be calculated by oscillating the target gazed by the subject and measuring how eyeball movement, saccade in particular follows the movement of the target, in the similar manner of evaluating eye fatigue on the basis of mutual correlation of time differential of movement of both eyes, proposed by Seiji Yoshino et al. If the eyeball movement completely follows the movement of the target, the fraction dimension is 1.

Further, according to W. N. Charman: "Fluctuations in accommodation: a review" Opthal. Physiol. Opt., 1998, 8, pp. 153-164 there is a small oscillation movement (small movement in accommodation) corresponding to small involuntary movement or flicks in eyeball movement with respect to accommodation also, and such movement is regarded as noise. Thus, fractal dimension of small oscillation may be analyzed by employing the present invention.

In addition, according to S. F. Stanten & L. Stark: IEEE.,BME-13, pp. 140-152, 1966, a noise component that always exist at a frequency of approximately 2 Hz of a normal pupil movement is confirmed, and fractal dimension of such a noise component may be calculated. A pupil system is controlled by autonomic nervous system and is available for evaluations (quantifications) in diagnosis of mental disease or curative effects of various internal medicine diseases as well as in a field of ophthalmology.

Figure 6:
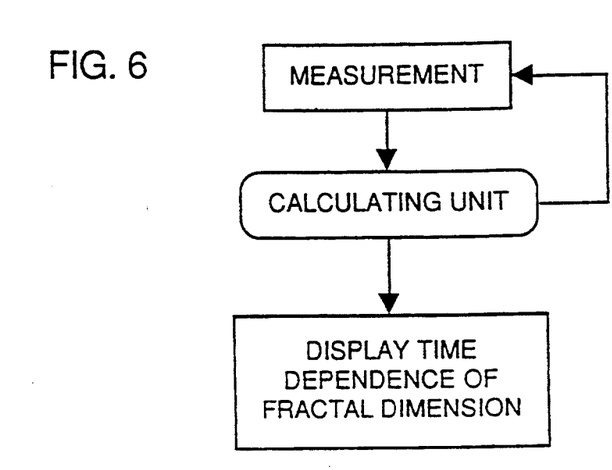
FIG. 6 is a flow chart showing the operation of another embodiment of the present invention.

FIG. 6 is a flow chart showing a further embodiment of the present invention. In the embodiment shown in FIG. 6, the steps of input of eye movement data to calculation of the fractal dimension shown in FIG. 4 are used, time dependence of the fractal dimension is analyzed with respect to each of the eyeball control systems simultaneously, and an overall index of eyeballs is obtained as a system from each correlation relationship. That is, data is sampled at appropriate time intervals, fractal dimension is calculated on the basis of the data of the time intervals, and as a result of calculation at each time interval, time is plotted on the abscissa and the fractal dimension is plotted on the ordinate.

Figure 7:
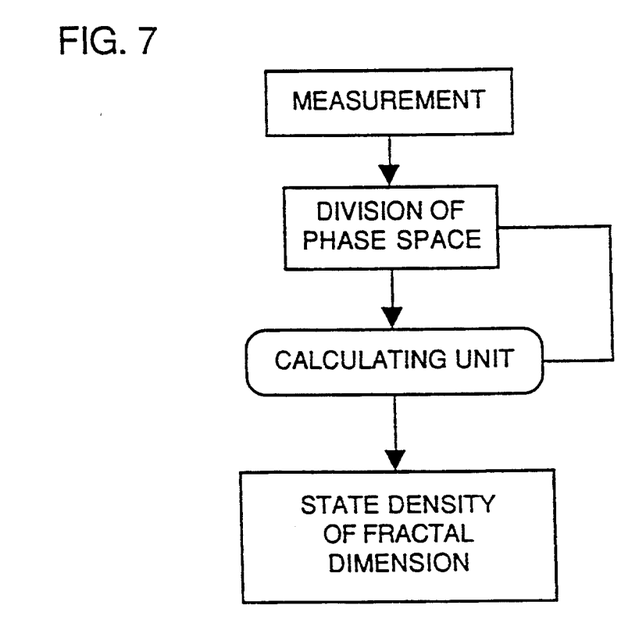
FIG. 7 is a flow chart showing operation of a still further embodiment of the present invention.

FIG. 7 is a flow chart showing still another embodiment of the present invention. In the embodiment of FIG. 7, distribution of fractal dimension in phase space is investigated by using an f (α) spectrum (T. C. Halsey et al.: Phys. Rev., A33 (1986), 1141) that features a multi-fractal structure as an expanded concept of fractal dimension.

In each of the foregoing embodiments, since the fractal dimensions are calculated with respect to the entire set of data points in phase space, a fluctuation of fractal dimension in each portion in phase space is neglected. In the multi-fractal structure, since distribution density of fractal dimension in phase space is taken into account, precise numerical representation is enabled. More specifically, as shown in FIG. 7, measurements of data points in phase space are carried out simultaneously, the phase space is divided into partial spaces, and the fractal dimension is calculated in each partial space. The histogram of the fractal dimension is plotted as a graph by output portion 6, in which the fractal dimension is plotted on the abscissa while the frequency thereof is plotted on the ordinate.

Figure 8:
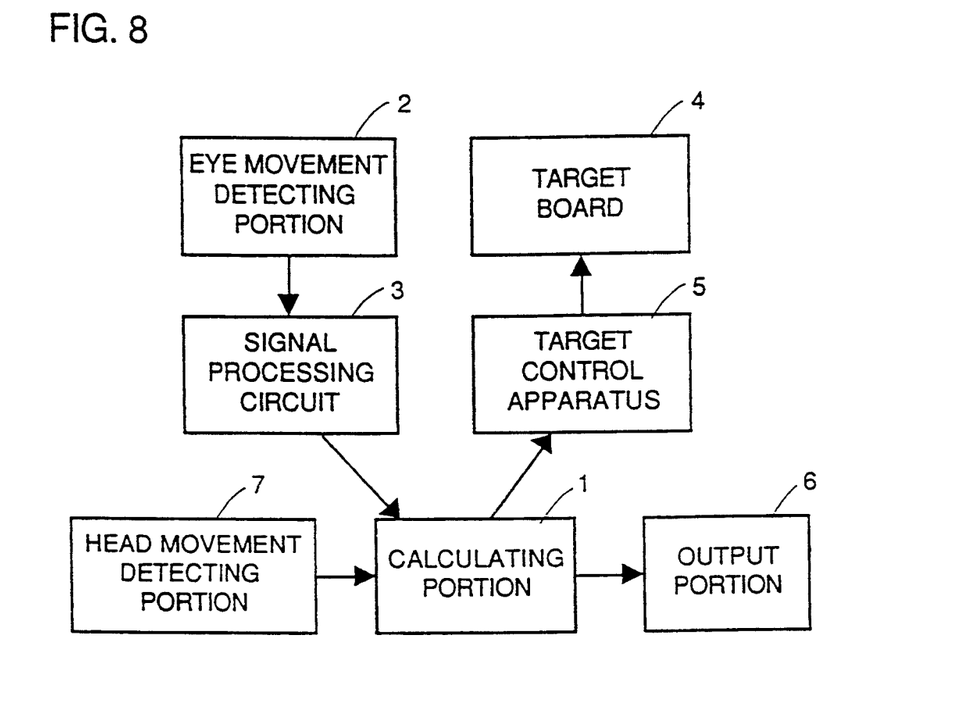
FIG. 8 is a schematic block diagram of a still further embodiment of the present invention.
Figure 9:
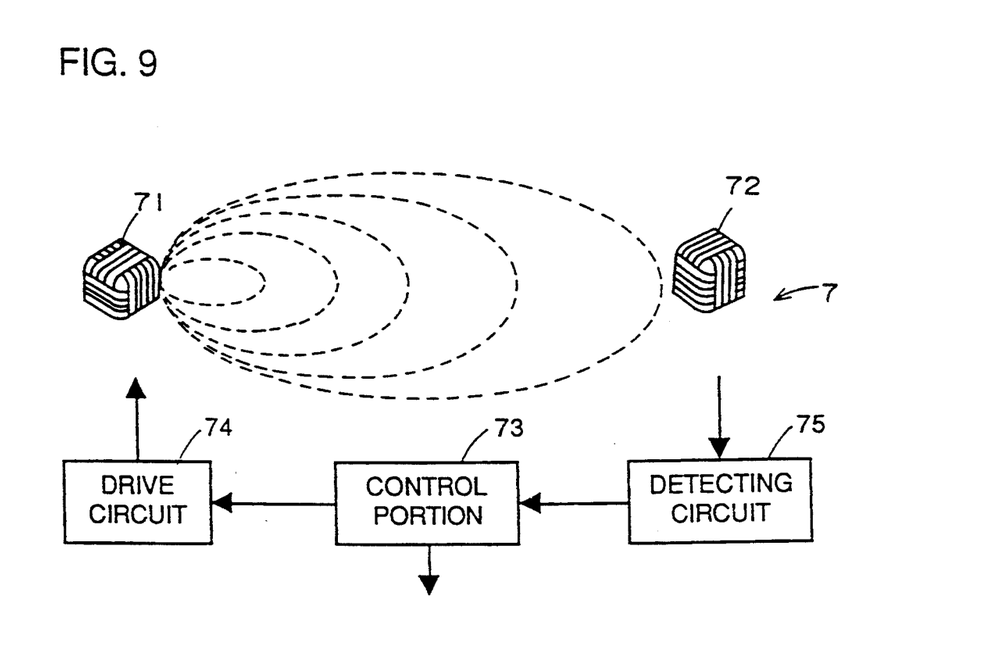
FIG. 9 shows a specific example of the head movement detecting portion shown in FIG. 8.

FIG. 8 is a block diagram showing a still further embodiment of the present invention and FIG. 9 shows a specific example of the head movement detecting portion shown in FIG.

In the embodiment shown in FIG. 8, a head movement detecting portion 7 for detecting the movement of the head of a subject is provided in addition to the structure of the embodiment shown in FIG. 1. The head movement detecting portion 7 is formed of a magnetic sensor as shown in FIG. 9. The head movement detecting portion 7 includes an orthogonal coil serving as a source 71 and an orthogonal coil serving as a sensor 72. The drive circuit 74 drives the orthogonal coil of the source 71 to generate a magnetic field in response to an instruction from a control portion 73. The sensor is attached to the goggles shown in FIG. 2 above, and when the subject wearing the head movement detecting portion 7 moves, a voltage is induced in the sensor 72, the voltage is detected by the detecting circuit 75 and the detected output is calculated by the control portion 73, so that data corresponding to the movement of the head is output.

Figure 10A:
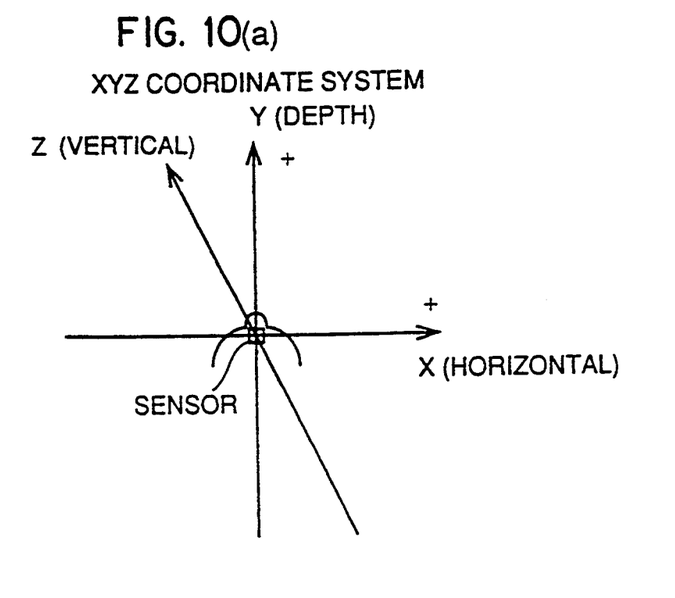
FIGS. 10(a) and 10(b) show a principal of the head coordinate system with the subject being the center.
Figure 10B:
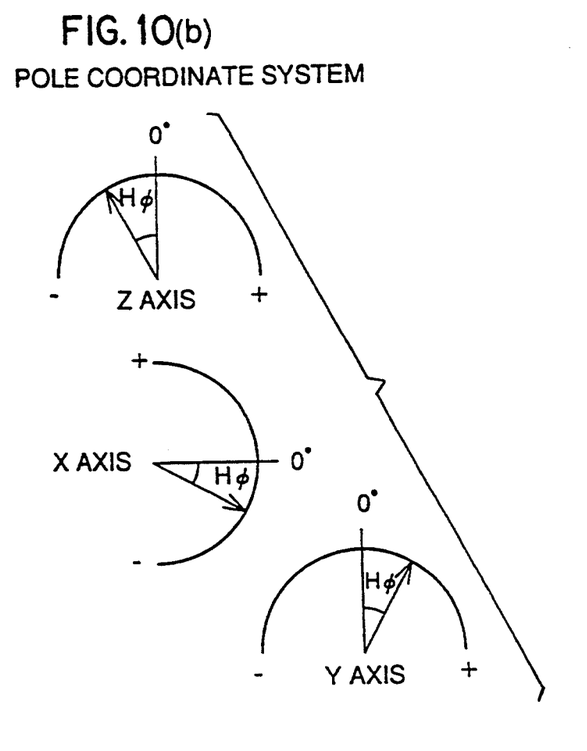

FIG. 10 is an illustration showing the principle of the head coordinate system with the subject being the center. Referring to FIG. 10, the head coordinate system detected by the head movement detecting portion 7 will be described. The head coordinate system includes two systems, that is, XYZ coordinate system realized by the translational movement of the subject with respect to the object of monitoring such as shown in FIG. 10(a), and a polar coordinate system based on the rotation movement of the head such as shown in FIG. 10(b). The amount of head movement in respective coordinate systems are defined as (Hx, Hy, Hz), (Hψ, Hφ, Hθ). In this embodiment, the direction toward the object of monitoring is represented by the Y axis, the horizontal movement is represented by the X axis and the vertical movement is represented by the Z axis, as an example. Hφ represents the rotation of the X axis, that is, the movement of one's neck upward or downward. Hθ represents the rotation of the Y axis, that is, the movement of inclining one's neck once from the left shoulder to the right shoulder. Hψ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations are obtained.

$$Ex = 180/\pi \cdot \tan^{-1} Hx / (D+Hy) \tag{1}$$

$$Ey = 180/\pi \cdot \tan^{-1} Hz / (D+Hy) \tag{2}$$

where D: distance from the subject to the point of gazing.

When the neck is inclined by Hθ to the left shoulder or to the right shoulder, the coordinate of the eye movement system rotates. Therefore, the eye movement coordinate system (Xe, Ye) inclined by Hθ must be changed to the coordinate system (Xe', Ye') which is orthogonal to the original object of monitoring.

$$Xe' = Xe \cdot \cos H\theta + Ye \cdot \sin H\theta \quad (3)$$

$$Ye' = -Xe \cdot \sin H\theta + Ye \cdot \cos H\theta \quad (4)$$

The movement of the line-of-sight (Xh, Yh) realized by the head movement is represented by the following equations (5) and (6) derived from the equations (1) and (2).

$$Xh = Ex + H\psi \quad (5)$$

$$Yh = Ey + H\phi \quad (6)$$

Therefore, the movement of the line-of-sight (vx, vy) taking the head movement into account is represented by the following equations (7) and (8), from equations (3) to (6).

$$Vx = Xe' + Xh \quad (7)$$

$$Vy = Ye' + Yh \quad (8)$$

By employing the equations (7) and (8) above, the ordinary movement of one's line-of-sight effected by combining head movement and eye movement can be reproduced.

Figure 11:
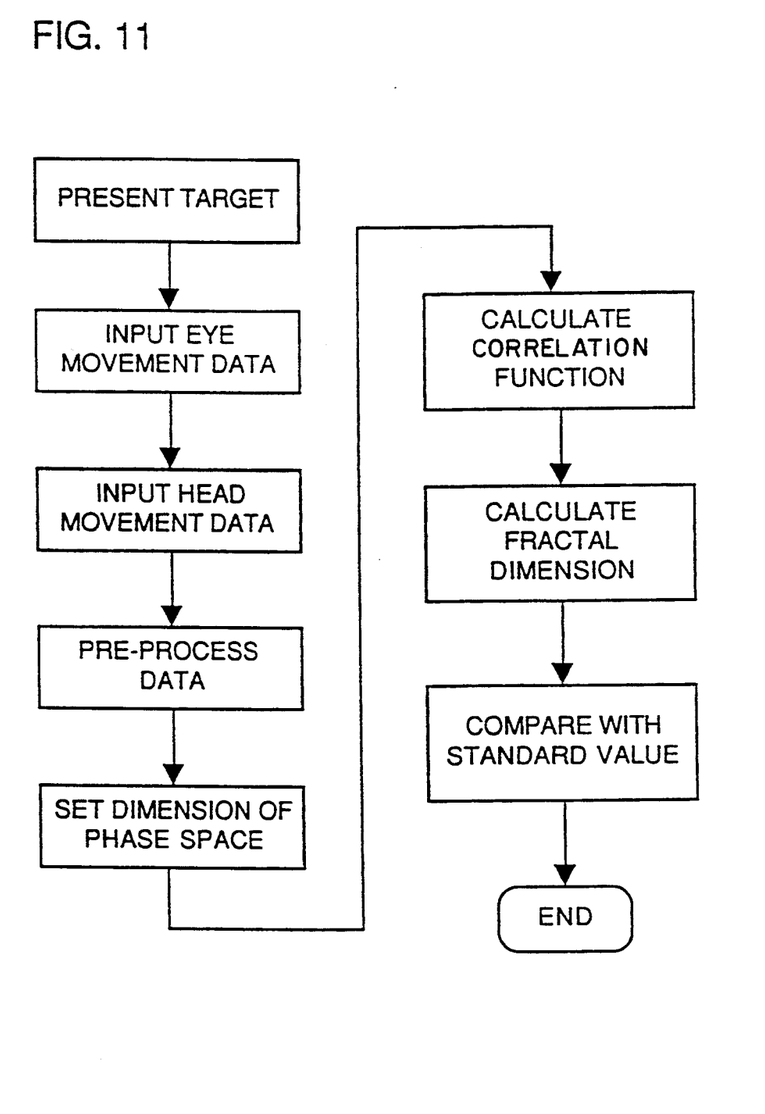
FIG. 11 is a flow chart showing the operation of a still further embodiment of the present invention.

FIG. 11 is a flow chart showing the operation of a yet another embodiment of the present invention.

The operation of this embodiment will be described with reference to FIGS. 8 to 11. In the similar manner as in the embodiment of FIG. 4, a target is presented by the board 4, eye movement data is input to calculating portion 1 from eye movement detecting portion 2, and thereafter, head movement of the subject is detected by the head movement detecting portion 7. Thereafter, as described with reference to FIG. 10 above, the overall movement of the line-of-sight (Vx, Vy) provided by combining the head movement and the eye movement is calculated by combining the result of detection of the eye movement Ex, Ey and the angle and the position of the head Hc, Hθ, Hφ and Hx, Hy and Hz. By using the values Vx and Vy, fractal dimension of each of the components of the small involuntary movement at various angles of gazing is calculated. The calculation is the same as that of FIG. 4. The measured values of various parameters are independently or totally evaluated as co-operated movement, which evaluation is used for discriminating Alzheimer's disease.

As described above, according to the embodiments of the present invention, a target is presented to a subject, eye movement of the subject at that time is detected, abnormality of small involuntary movement component is discriminated by using fractal dimension analysis on the basis of time-change of the movement of line-of-sight on the basis of the detected eye movement, so as to determine whether the disease is related to brain function. Therefore, troubles in the eye movement control mechanism in the brain of the subject can be easily detected, and Alzheimer's disease can be easily discriminated from cerebrovascular disease.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for detecting small involuntary eye movement for determining disease related to brain function by detecting eye movement of a subject, comprising:

eye movement detecting means for detecting a point of gazing by detecting eye movement of said subject;

target presenting means for presenting a target to said subject; and calculating means for discriminating abnormality of the small involuntary movement component by fractal dimension analysis, from time-change of a movement of line-of-sight base on the eye movement detected by said eye movement detecting means while said subject is gazing at the target presented by said target presenting means, for determining a disease related to brain function.

2. An apparatus for detecting small involuntary eye movement for determining disease related to brain function by detecting eye movement of a subject, comprising:

eye movement detecting means for detecting a point of gazing by detecting eye movement of said subject;

target presenting means for presenting a target to said subject;

calculating means for discriminating abnormality of the small involuntary movement component by fractal dimension analysis, from time-change of a movement of line-of-sight base on the eye movement detected by said eye movement detecting means while said subject is gazing at the target presented by said target presenting means, for determining a disease related to brain function; and head movement detecting means for detecting head movement of said subject, wherein said calculating means includes means for calculating the movement of the line-of-sight on the basis of detection output from said head movement detecting means and detecting output from said eye movement detecting means while said subject is gazing at said target, for discriminating abnormality in said small involuntary movement component on the basis of the movement of the line-of-sight.

3. The apparatus for detecting small involuntary movement according to claim 1, wherein said calculating means includes means for calculating small oscillation from the time-change of said detected movement of the line-of-sight, calculating the fractal dimension corresponding to the small oscillation, and for quantifying characteristics of an eyeball control system corresponding to the calculated fractal dimension.

4. The apparatus for detecting small involuntary movement according to claim 3, wherein said calculating means includes means representing said small oscillation as time-serial two dimensional data, setting dimension of phase space corresponding to the two dimensional data, and for calculating a correlation dimension corresponding to the set dimension of the phase space.

5. The apparatus for detecting small involuntary movement according to claim 3, wherein
said calculating means includes means for comparing said calculated fractal dimension with a predetermined standard value for determining a disease related to brain function.

6. The apparatus for detecting small involuntary movement according to claim 1, wherein
said calculating means includes means responsive to a detection output from said eye movement detecting means for determining small oscillation of each of the left and right eyeball control systems and for analyzing time dependence of fractal dimension of respective eyeball control systems simultaneously, corresponding to respective small oscillations.

7. The apparatus for detecting small involuntary movement according to claim 4, wherein
said calculating means includes means for dividing said phase space into partial spaces and for calculating fractal dimension of each of the partial spaces.

8. The apparatus for detecting small involuntary movement according to claim 2, wherein
said calculating means includes means for calculating small oscillation from the time-change of said detected movement of the line-of-sight, calculating the fractal dimension corresponding to the small oscillation, and for quantifying characteristics of an eyeball control system corresponding to the calculated fractal dimension.

9. The apparatus for detecting small involuntary movement according to claim 8 wherein
said calculating means includes means representing said small oscillation as time-serial two dimensional data, setting dimension of phase space corresponding to the two dimensional data, and for calculating a correlation dimension corresponding to the set dimension of the phase space.

10. The apparatus for detecting small involuntary movement according to claim 8, wherein
said calculating means includes means for comparing said calculated fractal dimension with a predetermined standard value for determining a disease related to brain function.

11. The apparatus for detecting small involuntary movement according to claim 9, wherein
said calculating means includes means for dividing said phase space into partial spaces and for calculating fractal dimension of each of the partial spaces.

* * * * *

UNITED STATES PATENT AND TRADEMARK OFFICE
CERTIFICATE OF CORRECTION

PATENT NO. : 5,365,941
DATED : November 22, 1994
INVENTOR(S) : Hiroshi YOSHIMATSU et al.

It is certified that error appears in the above-indentified patent and that said Letters Patent is hereby corrected as shown below:

On the title page, item [73] should read as follows:

-- ATR Auditory and Visual Perception Research Laboratories, Kyoto, Japan, Shinji Murakami, Mitsuru Fujii, Norihito Nakano, Jiro Miyazawa, Ryo Fukatsu, and Naohiko Takahata all of Hokkaido, Japan--

Signed and Sealed this

Twenty-ninth Day of August, 1995

Attest:

BRUCE LEHMAN

*Attesting Officer*     *Commissioner of Patents and Trademarks*